United States Patent [19]

Tack et al.

[11] Patent Number: 5,046,355

[45] Date of Patent: Sep. 10, 1991

[54] PROCESS FOR ASSESSING COLD START PERFORMANCE OF A WAX CONTAINING FUEL

[75] Inventors: Robert D. Tack, Abingdon; Sean A. Creedon, Derby, both of United Kingdom

[73] Assignee: Exxon Chemical Patents Inc., Linden, N.J.

[21] Appl. No.: 401,252

[22] Filed: Aug. 31, 1989

[30] Foreign Application Priority Data

Sep. 8, 1988 [GB] United Kingdom ................ 8821079

[51] Int. Cl.$^5$ .......................................... G01N 31/02
[52] U.S. Cl. .................................................. 73/61.4
[58] Field of Search ...................... 73/61 R, 61.2, 61.4, 73/61.1

[56] References Cited

U.S. PATENT DOCUMENTS

| | | | |
|---|---|---|---|
| 3,208,267 | 9/1965 | Schatzberg | 73/61 R |
| 3,872,710 | 3/1975 | Louvel | 73/61.4 |
| 3,945,243 | 3/1976 | Ouvrard | 73/61.4 |
| 4,357,667 | 11/1982 | Skarlos | 73/61 R |

FOREIGN PATENT DOCUMENTS

| | | |
|---|---|---|
| 0030099 | 11/1980 | European Pat. Off. . |
| 0156577 | 3/1985 | European Pat. Off. . |
| 2215136 | 8/1974 | France . |
| 1418431 | 12/1975 | United Kingdom . |
| 2043246 | 10/1980 | United Kingdom . |

OTHER PUBLICATIONS

Journal of the Institute of Petroleum, vol. 52, No. 510, Jun. 1966, pp. 173-185.

Primary Examiner—Robert Raevis
Attorney, Agent, or Firm—V. T. White

[57] ABSTRACT

Cold start performances in an engine of a wax-containing fuel may be assessed by drawing said fuel from a container under standardized conditions through a filter and measuring the rate of flow of fuel past said filter and comparing said flow rate with a flow rate obtained under the same conditions with a fuel of known cold start performance. This provides a relatively quick and simple indication of whether an engine running on such a fuel at the test temperature might be expected to have its filter blocked by the wax, preventing it from starting.

7 Claims, 2 Drawing Sheets

Non-critical fuel system          Critical fuel system

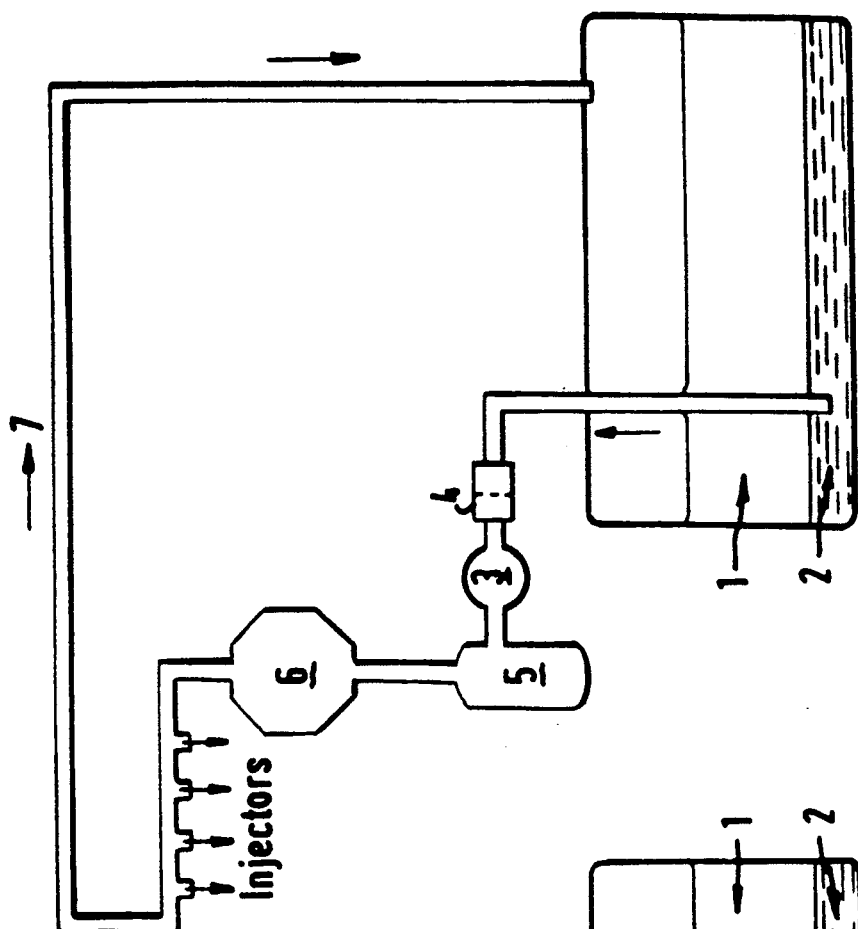
FIG.1A Non-critical fuel system
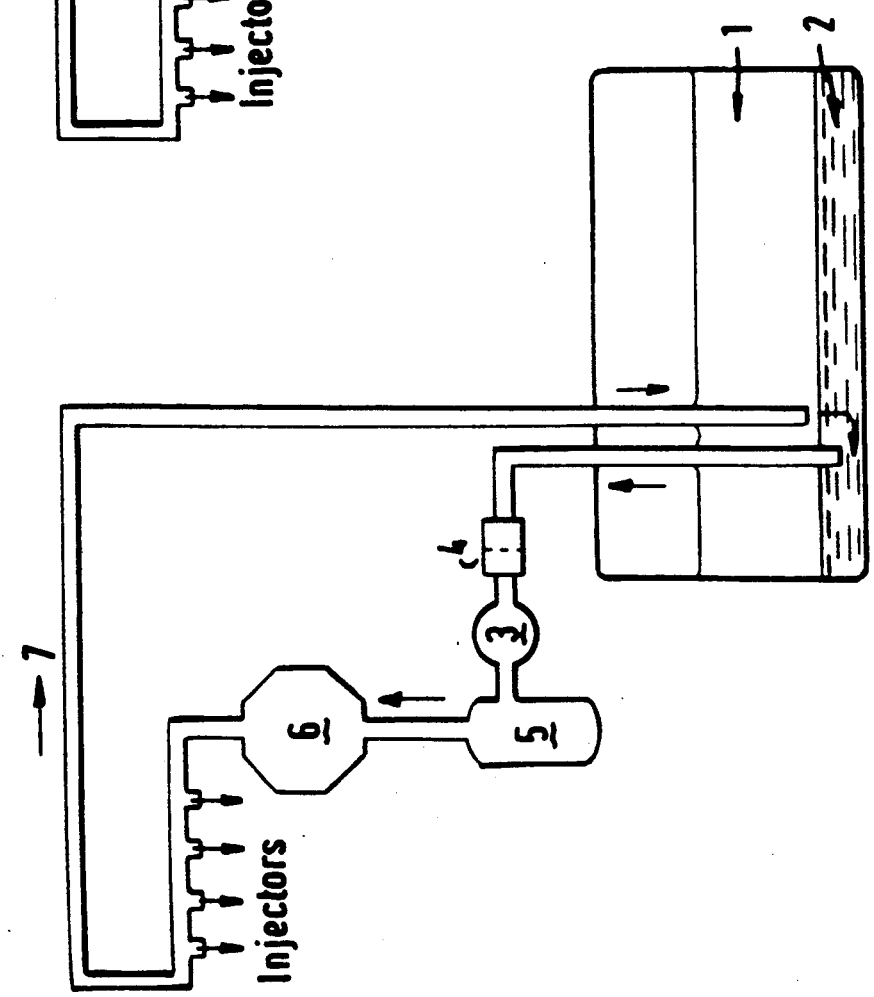
FIG.1B Critical fuel system

PROCESS FOR ASSESSING COLD START PERFORMANCE OF A WAX CONTAINING FUEL

The present invention relates to a process for assessing or predicting the cold flow performance of a distillate petroleum fuel, in particular a middle distillate or diesel fuel, in a diesel vehicle whose fuel system design is such that the engine may not start when cold because of wax building up on the filter between the fuel tank and the engine.

Crude and refined petroleum fuels, e.g. diesel fuel, contain ranges of n-alkanes that separate out as solid wax at temperatures below the fuel cloud point. For example, when a 0° C. cloud point diesel fuel is cooled below 0° C., e.g. during a cold spell in winter, the wax crystallizes out to form plate-like crystals that gel the fuel and prevent its passage through filters and narrow pipes. To lower the temperature at which wax crystallization limits the use and distribution of such fuels, certain wax crystal modifying additives are included in fuels to reduce the size and alter the shape of the wax crystals formed. For example, it is common practice to add to diesel fuels low molecular weight copolymers of ethylene and unsaturated esters, in particular ethylene-/vinyl acetate copolymers. Using such additives, plate-like wax crystals of about 0.5 to 5 millimeters in size which would otherwise form, may be replaced by the formation of elongated pyramid-like crystals which are about 20 to 50 microns in length. As a result of using such additives, the fuel no longer gels and may still be used at temperatures several degrees below the cloud point i.e. the fuel will flow and most diesel vehicles will continue to operate at these lower temperatures in the presence of these modified wax crystals.

To assess the performance of a fuel at low temperatures, a test is carried out to measure the temperature at which the crystallized wax blocks or plugs the filter. This temperature is known as the Cold Filter Plugging Point (CFPP). Many countries set standards for CFPP which must be met by oils and fuels. The Cold Filter Plugging Point Test (CFPPT) is carried out by the procedure described in detail in "Journal of the Institute of Petroleum", Volume 52, Number 510, June 1966, pp. 173-185.

A tube of a 40 ml sample of the fuel to be tested is cooled in a bath which is maintained at about −34° C. which will cause non-linear cooling at about 1° C./min. When the fuel reaches a temperature of at least 2° C. above its cloud point the cooled fuel is tested for its ability to flow through a fine screen in a prescribed time period. The test device is a pipette to whose lower end is attached an inverted funnel, which is positioned below the surface of the fuel to be tested. Stretched across the mouth of the funnel is a 350 mesh (45 micron) circular screen having a 12 millimeter diameter. The test is carried out by applying a vacuum to the upper end of the pipette to draw 20 ml of fuel through the screen up into the pipette. After a successful test the fuel is returned immediately to the tube. This test is repeated with each one degree drop in temperature until the fuel fails to fill 20 ml of the pipette within 60 seconds. This failure temperature is the CFPP temperature. The difference between the CFPP of an additive free fuel and of the same fuel containing an additive is reported as the CFPP depression by the additive. The greater the CFPP depression for a particular concentration of additive, the more effective the additive is as a flow improver.

The CFPP test is intended to predict for each fuel the temperature above which most diesel vehicles will have no operability problems due to cold flow. However, some vehicles with particular fuel system designs may experience problems above the CFPP.

These problems may be exacerbated by the settling of the wax crystals in the fuel storage tank. Prolonged storage of diesel fuel in exposed tanks at sub-cloud point temperatures, e.g. 10° C. below the cloud point, will result not only in wax crystallization but, if the fuel remains static (e.g. in a vehicle parked over a cold weekend), then the wax crystals will settle and agglomerate at the base of the fuel storage tank. To alleviate this problem a wax anti-settling agent (WASA), e.g. as described in EP-B-0030099, may be added to the fuel.

BRIEF DESCRIPTION OF DRAWINGS

FIGS. 1-1B is a critical fuel system.

Figure 2:
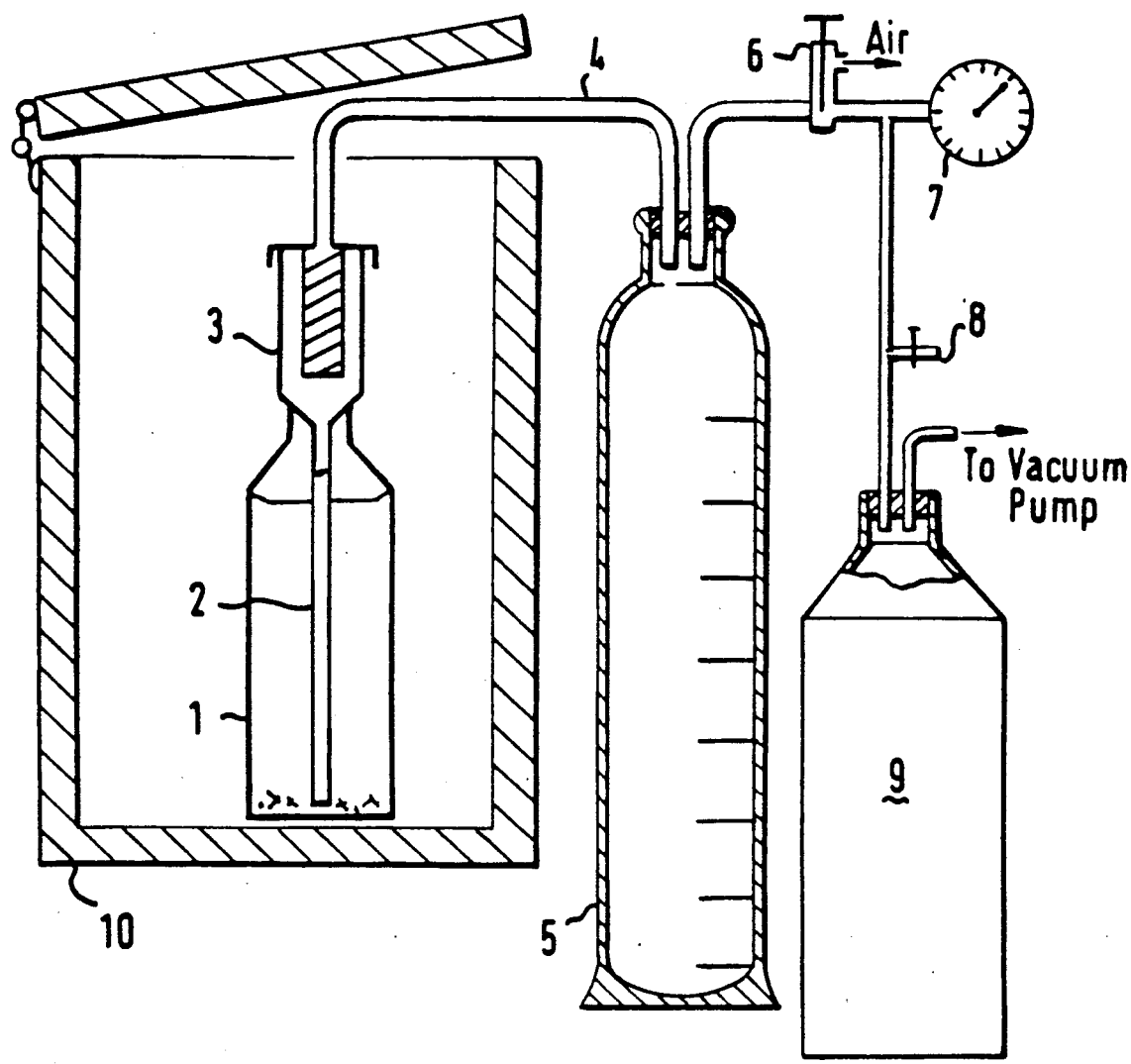
FIG. 2 is an apparatus to carry out the process.

Factors that make a diesel vehicle fuel system susceptible to failure at unexpectedly high temperature due to filter waxing (a "critical" system) are:
a small filter, in an exposed location
a high fuel recirculation rate
hot return fuel line positioned remote from the offtake.
These factors can be appreciated on examination of diesel fuel systems such as are illustrated in FIG. 1. Fuel system A is non-critical. In this system on start-up after a long cold period, fuel 1 containing the settled wax 2 is drawn by the lift pump 3 through the prefilter 4 into the main filter 5 where it is trapped and builds up a thick layer of wax crystals which are not small enough to pass the filter. Fuel passes through the injector pump 6 where it gets heated up. More fuel is pumped than is needed by the engine and the excess, warm fuel is recirculated via conduit 7 to the fuel tank. In a non-critical system, the warm recirculated fuel is returned close to the take off point where it redissolves the wax in the fuel being drawn off. The warm return fuel may even be mixed with the cold fuel in a swirl chamber. Within about 10 to 15 minutes the warm fuel starts to redissolve the waxy build up on the main fuel filter, removing any hindrance to the fuel flow.

Fuel system B in FIG. 1 is a critical fuel system, in which the recirculated fuel is returned to the tank in a position remote from the take off point. This means that it is a long time before heat from the recirculated fuel can redissolve any wax on the main filter. In addition, such systems may also have high recirculation rates and small filters, making them particularly susceptible to the build up of wax which can, eventually, block the flow of fuel to the engine, leading to failure.

A comparison of a non-critical fuel system, A, with a critical system, B, is made in Table 1.

TABLE 1

| Vehicle | A | B |
|---|---|---|
| Engine Rated Power, kW: | 37 | 246 |
| Usable filter area (cm/kW): | 128 | 13 |
| % of fuel recirculated to tank: | 70 | 90 |

Vehicle B, having a larger engine and a higher recirculation rate, draws more waxy fuel in the same time through a smaller filter than vehicle A, and returns the fuel to a position remote from the take off point. As a result, vehicle B has problems above the fuel CFPP, while vehicle A fails at or below the CFPP.

Previously, to determine failure point in an engine, particularly coldstart of an engine with a critical fuel system and with settled wax in the tank, it was necessary to carry out field trials or Cold Climate Chassis Dynamometer (CCCD) tests on diesel vehicles. Such testing is expensive, time consuming and slow. There was therefore a need for a simple laboratory test for a fuel which would indicate whether or not the fuel would cause an engine to fail at a particular temperature.

Preferably such a test would provide a pass/fail result and a means of comparing the effectiveness of different additives or different treat levels of the same additive. The present invention provides a method which may be carried out in a laboratory, the pass/fail results of which surprisingly show good correlation with the pass/fail of an engine used in a field trial or run in the CCCD.

Thus the present invention provides a method for assessing cold start performance in an engine of a wax-containing fuel, which comprises drawing said fuel from a container under standardized conditions through a filter, and measuring the rate of flow of fuel past said filter, and comparing said flow rate with a flow rate obtained under the same conditions with a fuel of known cold start performance, the standardized conditions being conditions of temperature, pressure under which the fuel is drawn, filter dimensions and permeability (in terms of capture size), and position in the fuel container from which the fuel is drawn.

The temperature at which the method is carried out is generally 5° to 15° C. below the cloud point of the fuel, since it is within this range that an engine typically fails. This temperature is preferably reached by cooling the sample from 5° C. or more above the fuel cloud point at a rate of 0.1° to 6.0° C./hour, more preferably about 2° C./hour, to the test temperature.

Once the test temperature is reached the fuel is generally held at that temperature for at least 2 and a half hours, preferably at least 3 hours. This allows the fuel to equilibrate at that temperature and for wax crystals to form and settle.

The fuel is usually drawn from its container under an absolute pressure of more than 0.5 atmosphere typically 60 kPascal (0.6 atmospheres). The reduced pressure causes the fuel to be drawn through the filter and into a graduated collection vessel. This pressure compares with the approximate maximum pressure drop across the main fuel filter before failure in a diesel vehicle engine. However, other pressures may be used to match the need; a lower absolute pressure (greater pressure drop) would make the test less severe, while a higher absolute pressure (lower pressure drop) would make the test more severe.

The wax in the fuel may settle, in which case there will be less wax at the top of the fuel and more wax at the bottom. It is preferred, therefore that the fuel should be drawn from the bottom of the container, as it would be if it were fuel drawn from the fuel tank on a diesel vehicle, ensuring that wax that has formed is drawn into the filter. Typically the container used will be cylindrical and it should be ensured that it has a reasonable height/diameter ratio; if this is too low (e.g. if 1 liter of fuel were in a 5 liter can) settled wax may not be picked up and variable results are obtained. A typical, cylindrical, commercial 1 liter can has height/diameter ratio of approximately 2/1, and is suitable for use in the method.

The fuel is preferably drawn vertically upwards through the filter. In general the filter is held vertically in a filter holder. The fuel enters the filter holder through the bottom, passes through the filter and out through the top of the holder. This ensures that no air bubbles are trapped, which would cause variations in the amount filter surface area used. To ensure both that wax is drawn from the bottom of the container and that the fuel passes vertically upwards through the filter, the filter holder has a dip tube that in use generally has its opening at the bottom of the fuel sample. The filter and filter holder should also be at the test temperature so that the wax does not melt on the filter.

The filter permeability is generally within the range of particle capture sizes 0.2 to 50 micron, preferably 2 to 25 micron. This may be fabricated out of a metal woven mesh, e.g. a "Dutch" weave, or a multilayer (depth) filter of paper or propylene or glass fibres, or similar material that is resistant to hydrocarbon solvents, bound together by a similarly insoluble resin.

The rate at which fuel passes through the filter may be measured by collecting the fuel in a graduated measuring cylinder on the far side of the filter from the fuel container and noting the volume collected at each passing minute, usually up to 5 minutes. It is this rate which is compared between fuels to indicate their relative qualities; it may also be expressed in terms of volume collected in a given time, e.g. in 5 min. if a 8 micro Gamma filter is used. Thus the flow rate may be expressed as an amount collected in a given time or as the time taken to collect a given amount.

The volume of the tube connecting the top of the filter to the measuring vessel and which carries the filtered fuel must be kept to a minimum, and kept constant within any series of comparative tests, because the volume of fuel held in this tube is not measured in the test.

The present invention also provides apparatus for carrying out this process, which comprises:
1) A fuel container capable of being cooled
2) An assembly for drawing fuel from the container which comprises a dip tube and a filter, and
3) Means for measuring the amount of fuel which passes through the filter.

The cooling means for the container may be e.g. a cold box, preferably with programmed cooling to ensure that the temperature of the fuel in the container is adequately controlled.

Apparatus suitable for carrying out the present process is show in FIG. 2.

The fuel is held in container 1, which holds e.g. 1 liter of fuel. A dip tube 2 reaching to the bottom of the fuel sample leads from the container to a filter 3 and from there via a connecting tube 4 to a measuring cylinder 5. The measuring cylinder is typically the same volume as the fuel container e.g. 1 liter. The measuring cylinder leads via a two-way tap 6 to T-pieces carrying a needle valve 7 which is used to control the pressure and a vacuum gauge 8, then to a buffer vacuum vessel 9 connected to a vacuum pump (not shown). The fuel container, dip tube and filter are within a cold box, 10, which is preferably a box with programmed cooling.

EXAMPLE

Using the apparatus shown in FIG. 2 a 1 liter container was filled with filtered fuel. An 8 micron, Whatman Gamma-12 filter was put in the filter holder and the container, dip tube and filter assembly were placed as shown in a cold box set at 5° to 10° C. above the cloud point of the fuel. After 2 hours at that temperature the cold box was programmed to cool the fuel sample at a rate of 2 deg.C/hour down to the test temperature.

Once the test temperature was reached, the fuel was left for a minimum of 3 hours (typically 3 to 6 hours) to allow the fuel to equilibrate at that temperature to allow for settling of wax crystals formed. This resting time is known as the "cold soak" time. If the effect of wax settling is a particular subject of interest, then the soak time may be extended to e.g. 1 day.

The vacuum, 0.4 atmospheres absolute pressure, is then turned on drawing fuel including crystallised wax to the filter and through to the measuring cylinder. The volume of fuel collected in the measuring cylinder is noted every minute up to a total of 5 minutes.

Collection of more than 0.4 liter of filtered fuel in five minutes is considered a "pass", whereas a collection of less is considered a fail. For comparative testing, it is recommended that a series of temperatures be covered in the testing of each sample to determine its expected operability temperature.

Table 2 shows a comparison of results obtained using a critical vehicle on a CCCD. It can be seen that the "pass" temperature of the present test correlates with an engine running on that fuel at that temperature being able to start from cold and that failure point of the present test correlates with failure of an engine to start from cold.

TABLE 2

COMPARISONS OF WAXED FILTER BLOCKING TEST AND CCCD RESULTS ON A CRITICAL VEHICLE

| | Wax Filter Blocking Test Volume through 25 micron in 2 min | | | | CCCD Result |
|---|---|---|---|---|---|
| | Fuel cl collected at: | | | Pass/Fail | Pass/Fail |
| Fuel | −10 | −14 | −18 deg. C. | Temperature | Temperature |
| A + 100 ppm EVAC1 | 13 | 10 | — | —/−10 | −7/−9 |
| A + 380 ppm EVAC1 | 50 | 23 | — | −10/−14 | −9/−11 |
| A + 100 ppm EVAC1 + 240 ppm WASA1 | 53 | 32 | — | −10/−14 | −13/−17 |
| B + 0.1% EVAC2 | 12 | 7 | — | —/−10 | —/−9 |
| B + 0.1% WAFI1 | 76 | 41 | 16 | −14/−18 | −15/— |
| B + 0.1% WASA2 | 75 | 60 | 65 | −18/— | −17/−21 |

| | Waxed Filter Blocking Test Volume through 8 micron in 5 min | | | | CCCD Result |
|---|---|---|---|---|---|
| | Fuel cl collected at: | | | Pass/Fail | Pass/Fail |
| Fuel | −9 | −11 | −13 deg.C | Temperature | Temperature |
| A + 500 ppm EVAC1 | 100 | 49 | 13 | −11/−13 | −11/−13 |
| C + 1000 ppm WAFI1 | 49 | 30 | 20 | −9/−11 | −9/−11 |
| D + 800 ppm EVAC2 | 66 | 20 | | −9/−11 | −12/−13 |
| D + 900 ppm WAFI2 | | | | −11/−16 | −11/−14 |

Table 3 gives details of the fuels used in this and the following tests.

TABLE 3

| | FUEL PROPERTIES (DEG. C.) | | | | |
|---|---|---|---|---|---|
| | Cloud | Distillation (ASTM D-86) | | | |
| Fuel | Point | IBP | 20% | 90% | FBP |
| A | −5 | 154 | 216 | 331 | 361 |
| B | 2 | 205 | 247 | 339 | 374 |
| C | −2 | 166 | 245 | 338 | 367 |
| D | −6 | 166 | 231 | 325 | 348 |
| E | −4 | 154 | 216 | 332 | 365 |

Additives used were commercial, Ethylene/Vinyl Acetate Copolymer (EVAC) based Middle Distillate Flow Improvers and commercial Wax Anti-Settling Additives (WASA) or Wax Anti-settling Flow Improvers (WAFI).

Tables 4 and 5 show the effects of variations in the waxed filter blocking test.

TABLE 4

CONDITIONS:
Collection time for 8 micron filter was 5 minutes, for 25 micron filter was 2 minutes

| Filter micron capture size: | 25 | 8 | 8 | 8 | 8 | 8 | 8 | 8 | 8 |
|---|---|---|---|---|---|---|---|---|---|
| Cooling deg. C./h | 2 | 2 | 2 | 4 | 4 | 5 | 5 | 5 | 10 |
| Test Temp. Deg. C. | −18 | −18 | −14 | −14 | −18 | −18 | −18 | −16 | −14 |
| Sample, Liter | 1 | 1 | 0.5 | 0.9 | 0.5 | 0.9 | 0.5 | 0.9 | 0.9 |
| RESULTS (centiliters) Fuel E with: | | | | | | | | | |
| EVAC1 | 23 | 18 | 20 | 32 | 15 | 23 | 19 | 35 | 80 |
| WAFI2 | 81 | 46 | 45 | 55 | 24 | 21 | 29 | 34 | 70 |

TABLE 4-continued

CONDITIONS:
Collection time for 8 micron filter was 5 minutes,
for 25 micron filter was 2 minutes

| WASA2 | 100 | 100 | 50 | 80 | 50 | 80 | 50 | 80 | 80 |

TABLE 5

Conditions:
Collection time for 2 micron filter was 5 minutes,
for 25 micon filter was 2 minutes

| | | | Mesh. | Mesh. |
|---|---|---|---|---|
| Filter micron capture size: | 2 | 2 | 25 | 25 |
| Cooling deg. C./h | 2 | 4 | 2 | 4 |
| Test Temp. deg. C. | −14 | −14 | −18 | −18 |
| Sample, liter | 0.5 | 0.9 | 0.9 | 0.9 |
| Results (centiliters): Fuel E with: | | | | |
| EVAC1 | 23 | 17 | 12 | 80 |
| WAFI2 | 34 | 25 | 20 | 90 |
| WASA2 | 50 | 80 | 90 | 90 |

Filters used were Gamma-12 filters, glass fibre bonded with a resin to high specification, except "Mesh" was Dutch weave wire mesh filter fabricated to fit in Gamma-12 filter holder.

It can be seen that performance of these fuels in a critical vehicle was better with WASA2 than with WAFI2 and both WASA 2 and WAFI 2 performed better than EVAC1.

These results show that for these fuels:
1. Between 0.5 and 1.0 liter, sample size is not critical.
2. Of commercially readily available filters a 25 or 8 micron Gamma filter may be used, the 8 micron being more severe so needs to take more time to collect fuel. The 2 micron filter allows too little differentiation between samples to give meaningful results.
3. The test allows rates of cooling up to around 5° C./hour with the Gamma-12 filters whilst retaining the differentiation between fuels, but at higher rates (e.g. 10° C./h) differentiation is lost.
4. A mesh filter, of the same dimensions may be substituted for the Gamma filter, to give similar differentiation but greater sensitivity to cooling rate.

On varying filter size this was found most suitable because large filters, e.g. as found on a diesel vehicle, needed about 5 liter of fuel for waxing problems to become apparent; smaller filters restricted fuel flow severely in the presence of wax so that little or no differentiation was found.

Table 6 shows the effect of wax settling. Pairs of 0.9 liter samples were cooled at 2° C./hour to −14° C. and held there for 1.5 days before testing to allow wax to settle. Then the test procedure as described above was carried out using an 8 micron Gamma-12 filter.

TABLE 6

| | cl Collected in 5 min. | |
|---|---|---|
| Fuel E with: | Sample settled | Sample shaken |
| EVAC1 | 16 | 329 |
| WAFI1 | 58 | 77 |
| WASA2 | 80 | 80 |

This shows how the settled wax can worsen the flow rate of the fuel, as is sometimes observed in critical vehicle operation. EVAC1 treated fuel gave wax settling, the settled wax blocking the filter much more than the same amount of wax when dispersed in the fuel by shaking just before the test. WAFI1 is better since this gives a small amount of wax settling and the deterioration in fuel performance for the settled sample is therefore small. WASA2 gives excellent wax dispersion and the same good result in both settled and shaken samples.

We claim:
1. A method for assessing the cold start performance in an engine of a wax-containing fuel, which comprises:
    (a) cooling said fuel in a container to a test temperature;
    (b) drawing fuel from the container through a filter, said filter also being at the test temperature;
    (c) measuring the rate at which the cooled test fuel flows through the filter;
    (d) performing steps (a), (b) and (c) above on a fuel of known cold start performance under the same and standardized conditions of test temperature, of the differential pressure across the filter, of filter dimensions and permeability, and of position in the container from which the fuel is drawn; and
    (e) comparing the rate measured for the test fuel with that measured for the fuel of known cold start performance.
2. A method according to claim 1 in which the filter is a 6 to 15 micrometer mesh.
3. A method according to claim 1 in which the absolute pressure under which fuel drawn is more than 50 kPa.
4. A method according to claim 1 in which the temperature of the fuel is 5° to 15° C. below the cloud point of the fuel.
5. A method according to claim 1 in which, prior to drawing, fuel has rested in the container for at least 2 and a half hours.
6. A method according to claim 5 in which prior to resting the fuel has been brought to the test temperature from at least 5° C. above its cloud point at a rate of 1° to 3° C./hour.
7. An apparatus using the method of claim 1 for assessing the cold start performance in an engine of a wax-containing fuel comprising:
    (a) a fuel receptacle;
    (b) means for cooling fuel contained in the receptacle to a test temperature;
    (c) means for drawing fuel at the test temperature from the receptacle;
    (d) a filter arranged so that fuel drawn from the receptacle is drawn therethrough;
    (e) means for cooling the filter to the test temperature; and
    (f) means for measuring the rate of flow of the fuel through the filter.

* * * * *